United States Patent
Katakis et al.

(10) Patent No.: US 7,138,281 B2
(45) Date of Patent: Nov. 21, 2006

(54) FABRICATION METHOD OF MULTISENSORS CHIPS FOR DETECTING ANALYTES

(75) Inventors: Ioannis Katakis, Tarragona (ES); Monica Campas Homs, Tarragona (ES)

(73) Assignee: Universitat Rovira I Virgili, Tarragona (ES)

( * ) Notice: Subject to any disclaimer, the term of this patent is extended or adjusted under 35 U.S.C. 154(b) by 0 days.

(21) Appl. No.: 10/345,771

(22) Filed: Jan. 16, 2003

(65) Prior Publication Data
US 2004/0087052 A1    May 6, 2004

(30) Foreign Application Priority Data
Jan. 22, 2002    (ES) ................................ 200200129

(51) Int. Cl.
*H01L 21/00*    (2006.01)
(52) U.S. Cl. ..................... 438/1; 257/E21.158; 997/883
(58) Field of Classification Search ............... 438/14, 438/1, 17, 49; 977/702, 704, 883, 884, 899; 257/E21.158, E21.159, E21.174, E21.175
See application file for complete search history.

(56) References Cited

U.S. PATENT DOCUMENTS

2002/0171079 A1* 11/2002 Braun et al. .................. 257/40
2003/0203394 A1* 10/2003 Eichen et al. .................. 435/6

\* cited by examiner

*Primary Examiner*—Caridad Everhart
(74) *Attorney, Agent, or Firm*—Notaro & Michalos P.C.

(57) ABSTRACT

A method includes (a) putting a multielectrodic chip lithographed in a wafer that contains between 2 and 2000 individually polarisable electrodes, in contact with a solution or suspension that includes modified colloidal particles with a (bio)chemical recognition element; (b) applying to an electrode of the multielectrodic chip, a potential between −1 and +2V vs. Ag/AgCl saturated, for a period of time between 1 and 300 seconds; (c) washing the chip after this stage (b); and (d) repeat the steps (b) and (c) as many times as needed to deposit a (bio)chemical recognition element, same or different to the one or ones previously deposited, on each one of the electrodes of that chip. The method is applicable for the fabrication of multisensors, particularly in chips and arrays for analytical and diagnostic applications.

9 Claims, 3 Drawing Sheets

US 7,138,281 B2

FABRICATION METHOD OF MULTISENSORS CHIPS FOR DETECTING ANALYTES

FIELD OF INVENTION

In general, the invention relates to the deposition of an element and a chemical or biochemical recognition module on a substrate and, in particular, with a method to elaborate chips, multisensors, and arrays for clinical, environmental and food analysis or, for toxicity assays, identification of compounds in combinatorial processes and other applications in which multiple and fast analysis is necessary.

BACKGROUND OF THE INVENTION

In the last few years, great advances have been made in the development of chips (microelectronic devices) capable to characterise and identify analytes of interest. In general, a chip or multisensor for the detection of analytes is composed of a substrate over which is placed a plurality of individually addressable analysis sites (IAASs). Each IAAS includes a selectively immobilised specific receptor. This receptor can be of biological nature, for instance, antibody, enzyme, oligonucleotide, etc., or a living biological system, for example, cell, tissue, live organism, etc., or of chemical nature, for example, aptamer, imprinted polymer, zeolite, etc., which recognises the analyte that selectively binds to or interacts with that receptor. When a solution that contains a sample with one or several analytes is put in contact with a chip that has one or more binding sites that have modified IAASs with specific receptors for those analytes, a receptor-analyte interaction is produced on the corresponding IAASs and, consequently, the presence of those analytes can be deduced in the assay sample and their concentration can be quantified by appropriate transduction schemes.

Selective deposition of molecules on the IAASs is very important in industrial scale manufacturing of arrays (devices that have a repetitive microelectronic architecture) for genetic analysis, chemical sensors, enzymatic and affinity biosensors and, microinterfaces for direct communication between microelectronic devices and living beings (like, for example, the direct control by the nervous system of biomechanical implants).

One of the methods followed by the industry to manufacture oligonucleotide arrays includes the application of site-addressable techniques based on photolithographic activation. This photolithographic activation uses solid-phase chemical synthesis (in situ), that is compatible with fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. The resolution of this technique is of the order of 1 µm or even less (0.1 µm). It is ideally limited by the wavelength of radiation used for patterning of the array. The disadvantage of this technique is that there is no possibility for the control of quality of the synthesised probes and, consequently, a redundancy in the number of hybridisation sites is necessary to assure reliability.

Other approaches to produce biochips (arrays in which the immobilized molecule is biological) use different microfluidic contact and non-contact printing technologies, which allow dispensing volumes of liquids in the range of the nanoliter. These contact and non-contact printing methods have the advantage that the biochemical compounds can be preselected in compliance with quality control standards. However, the resolution of the method (density of points) is one or two orders of magnitude smaller than the photolitographic activation.

Electrochemical methods are cheaper than the above-mentioned strategies. These methods include the electrochemical copolimerization of pyrroles and modified oligonucleotides with pyrrole groups. Ideally, the resolution of these techniques is also limited by the photolitographic limit of the design of the array. Besides, these techniques also allow a previous selection of oligonucleotides based on their quality. Consequently, they are more advantageous than the techniques previously mentioned, but, maybe, require more time for their design and might present the drawback of non-selective deposition. In addition, liquid chemistry is used for the production, which is not a standard in the semiconductor industry.

Colloidal gold is adequate for the immobilisation of mercapto-modified molecules, which form dative bonds with the gold surface. The use of colloidal gold is known to immobilise enzymes in sensors through electrodeposition. Crumbliss and collaborators [Crumbliss et al. (1992), Biotechnology and Bioengineering, 40:483–490], combined glucose oxidase (GOx), peroxidase (HRP) and xanthine oxidase (XO) with colloidal gold and electrodeposited those conjugates in platinum or vitreous carbon applying +1,6V (vs. Ag/AgCl saturated) for 2 hours. These enzymatic electrodes gave an electrochemical response to the corresponding enzymatic substrates in presence of mediators of the ferrocene family. Through this study they demonstrated the utility of the colloidal gold as vehicle of biocompatible deposition appropriate for the elaboration of enzymatic electrodes. Yabuki and Mizutani [Yabuki S. and Mizutani F. (1995), Denki Kagaku, 63(7): 654–659] also conjugated GOx with colloidal gold and deposited the conjugate on vitreous carbon, gold and platinum, by means of the same process, and observed that the intensity currents were ten times smaller using platinum or gold than with vitreous carbon, probably due to the lesser quantity of adsorbed conjugate in the metallic electrodes. However, none of these previous articles mentions the possibility of selective deposition with micrometric or sub-micrometric resolution.

SUMMARY OF THE INVENTION

The aim of the present invention is to supply an alternative method for the elaboration of chips and arrays to detect analytes. The invention is based on the selectively addressed electro-deposition of (bio)recognition and/or transduction elements to certain IAASs placed over an electrodic surface and with photolitographic resolution. Such a method obtained from this invention allows to elaborate chips and arrays useful for the detection of several analytes in a sample of reduced volume, typically, equal or inferior to 1 µL and, preferably, inferior to 100 nL.

DETAILED DESCRIPTION OF THE INVENTION

Figure 1:
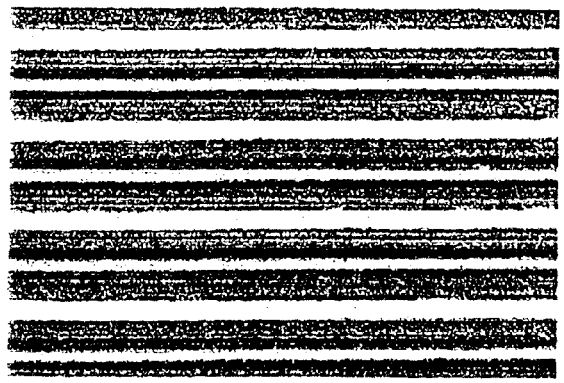
FIG. 1 is an optical microscope picture of an array of interdigitated electrodes on which can be observed the selective deposition of conjugates of colloidal gold (CG) with an oligonucleotide of sequence 5'-CCCCCCCCCCCCCTTTTTTTTTTTTTTTTTT CCCCCCCCCCCC-3'(SEQ ID NO: 1 in the accompanying "Sequence Listing") modified with fluorescein isothiocyanate (FITC) in 3' and a thiol group (SH) in 5'(FOT), as of now abbreviated as FOTCG, in the electrode of the array on which has been applied a potential (see Example 1). The grey lines correspond to the interspace between electrodes, the yellow ones to the electrode on which potential has not been applied, and the orange ones to the electrode on which potential has been applied.

The invention provides a method for the fabrication of a chip for the simultaneous analysis of several analytes, henceforth method of the invention, which comprises:
a) to put a multielectrodic chip, lithographed in a wafer, which has between 2 and 2000 individually polarizable electrodes, in contact with a solution or suspension that comprises modified colloidal particles with an element of chemical or biochemical recognition;
b) to apply to an electrode of that multielectrodic chip, a potential from −1 and +2V (vs. Ag/AgCl saturated) for a period of time between 1y 300 seconds, so that the element of chemical or biochemical recognition is deposited over that electrode on which potential has been applied;
c) to wash the chip after step b); and
d) to repeat steps a), b) and c) as many times a necessary to deposit a chemical or biochemical recognition element, equal or different to the one or the ones previously deposited, on each of the electrodes of that chip.

The multielectrodic chip properly designed, lithographed in a wafer of any standard size, that has between 2 and 2000 individually polarisable electrodes, serves as substrate on which is selectively deposited and with lithographic resolution the chemical or biochemical recognition element according to the present invention, and can be obtained by conventional methods of computer chips construction.

The colloidal particles included in that solution or suspension that is in contact with that multielectrodic chip constitute the base on which the chemical and biochemical recognition elements are joined to form the transduction and/or recognition nanometric modules. Illustrative examples of those colloidal particles are the gold, copper, silver, cadmium, glass, latex, polyurethane particles and, in general, any material, polymeric or not polymeric, known by the experts in the field. In a particular embodiment, those colloidal particles include gold colloidal particles of which preparation is described, for instance, in Crumbliss et al. (1992), Biotechnology and Bioengineering, 40:483–490.

The chemical or biochemical recognition element, henceforth, (bio)chemical recognition element, can be any compound of material that uses a chemical or biochemical mechanism to recognise the analyte that is selectively linked to a carrier nanoparticle, and the result is a (bio)recognition module appropriate to identify the analyte that is to be assayed. In an illustrative way, those (bio)chemical recognition elements can be chemical, biochemical or biological products, for example, aptamers, molecular tweezers, genetically modified enzymes, synthetic nucleic acids, crown esters, molecularly-imprinted polymers, enzymes, antibodies, nucleotide sequences, receptors, cells, and the like.

The (bio)chemical recognition element can be obtained through conventional techniques that are known by the experts in the field, for example, either from live sources, or through genetic engineering techniques or chemically.

Advantageously, that (bio)chemical recognition module is stabilised by adding a stabilising agent in order to avoid, for example, the colloids precipitation. In a particular performance, that stabilising agent is bovine serum albumin (BSA).

The (bio)chemical recognition element enters into a solution or suspension in a aqueous, organic or mixed environment (aqueous-organic) depending on the colloids stability in that environment.

According to the present invention, that (bio)chemical recognition module is selectively deposited on the electrode on which potential is applied. For the selective deposition of the (bio)chemical recognition module over an eletrode of that multielectrodic chip is applied a potential from −1 and +2V (vs. Ag/AgCl saturated) for a period of time between 1 and 300 seconds. Several assays have pointed out that, operating in such a way, it is possible to selectively deposit and with photolithographic resolution (bio)chemical recognition modules, in particular, colloidal gold conjugates with different (bio)chemical recognition elements of peptidic or polynucleotide nature joined with colloidal gold, on the electrodes on which potential is applied (see Examples 1–4), allowing the deposition of such (bio)chemical recognition elements in specific positions.

In a particular embodiment, the potential applied to the electrode is between -0.75 and +1.75V (vs. Ag/AgCl saturated), generally between −0.5 and +1.5V (vs. Ag/AgCl saturated), normally between −0.25 and +1.25V (vs. Ag/AgCl saturated), for example, between 0 and +1V (vs. Ag/AgCl saturated). In the same way, in a particular embodiment, the period of time during which the potential is applied to the electrode is between 1 and 200 seconds, generally between 1 and 100 seconds, normally between 1 and 50 seconds, for example, between 1 and 10 seconds.

The solvent used to suspend the (bio)recognition modules can be any solvent that stabilises the colloidal suspension, is compatible with the activity of the (bio)chemical recognition elements and allows electrode polarisation. In a preferred embodiment, the solvent is water with low salt or buffer concentration or ionic strength lower or equal to 0.3 M, for example 1 µM.

The (bio)chemical recognition element can be applied on the electrode using any conventional method or device, for example, using an appropriate microfluidic device. Despite of the fact that, the selective eletrodeposition of the (bio) chemical recognition element according to the present invention method uses chemistry in its liquid state, the method is completely compatible with the common testing processes and quality control in the microelectronic industry.

The resulting chip is washed through conventional techniques once the (bio)chemical recognition element has been selectively deposited the on the electrode. For this purpose, the previous solution is removed and the chip is dipped into a solvent that is compatible with the activity of the (bio) recognition element (in most cases deionised water) for 2 or 3 seconds. In a particular embodiment, when silicon wafers are used, as they are hydrophobic, once they have been removed from the water, in manufacturing conditions, can be considered that the wafer dries out within a few seconds. However, when a fluidic microsystem is used, washing will proceed changing the solvent in the micrometric conduits.

These stages of putting in contact a multielectrodic chip with a solution or suspension comprising modified collodial particles with a chemical or biochemical recognition element, selectively electrodepositing the (bio)chemical recognition module in the electrode on which potential is applied and of washing the chip are repeated until a (bio)chemical recognition element is deposited, equal or different in every case, on each of the present electrodes in the multielectrodic chip. Finally, the chips are cut off and packaged with conventional techniques.

The manufactured chips with the invention method can contain different (bio)chemical recognition elements, that is to say, different transduction and/or recognition nanometric modules, in each of the appropriate chips for the analyte or analytes to analyse. In an illustrative way, the chips fabricated according to the invention method can be used to assay sugars, for example, glucose, lactose, lactulose, etc., antigens, nucleotide sequences (they even allow to detect a single mutation in a nucleotide sequence), small molecules, etc.

Therefore, the invention method provides multisensors, chips or arrays useful for analytical applications in general, for example, to do chemical or biochemical analysis, with different applications, such as, biomedical (diagnosis), environmental, etc. These chips and arrays have a resolution limited only by the photolitographic limit of the design of the conductive surfaces of the chip (currently 0.1 µm approximately). Lately, it is foreseen that with the progress of the state of the technique of these methods, this limit will be imposed by the size of the (bio)chemical recognition colloid or module (1–10 nm).

Although the invention method allows to fabricate chips and arrays for analytical purposes, the use of the invention method is not recommended to fabricate large arrays of genes due to the minimum non-selective but accumulative depositions of the (bio)chemical recognition element that is produced in non-polarised electrodes. This percentage of non-selective depositions is less than 10% of the total of the depositions, which makes the invention method inadequate to fabricate large arrays of genes. However, the invention method is perfectly competitive to fabricate chips and arrays aimed for applications in which are analysed between 2 and 25 analytes and with the possibility of using sample volumes between 2 nL and 200 nL. These characteristics make the invention method adequate to fabricate chips for the majority of common assays in enzymatic or affinity diagnosis. The fact that the assay volume is small allows the use of sample acquisition methods that are minimally invasive, and permits routine diagnostic applications at home and tele-diagnosis.

An additional advantage of the invention method is that it allows selective deposition of the (bio)chemical recognition element, with photolithographic resolution, in short periods of time, generally between 1 and 5 minutes as every cycle of the invention method can be done in very low periods of time. In a particular performance, each cycle of the invention method can be done in periods of time less than 120 seconds, including the deposition and washing stages. Consequently, the fabrication process can be completed at speeds comparable to the contact and non-contact printing techniques.

The following examples illustrate the invention and should not be considered as indicating its limit.

EXAMPLE 1

This example illustrates the selective deposition of conjugates FOTCG in one of the electrodes that constitutes an interdigitated array. For this purpose, a solution of a FOTCG conjugate obtained according to the protocol described by Storhoff and collaborators [Storhoff et al. (1998), Journal of the American Chemical Society, 120:1959–1964], was put in contact with said interdigitated array and a +1.6V (vs. Ag/AgCl sat'd) potential was applied for two hours on half of the electrodes of the array. The selective deposition of these conjugates over the electrodes on which the potential was applied was characterised by optical microscopy. The results obtained are shown in FIG. 1 on which lines of different colours can be seen, specifically:

grey lines (5 µm of thickness), which correspond to the interspace between electrodes;

yellow lines (5 µm of thickness), which correspond to the electrode on which potential has not been applied; and orange lines (5 µm of thickness), that correspond to the electrode on which potential has been applied.

The difference in the colour shows the selective deposition of the conjugates.

EXAMPLE 2

Figure 2:
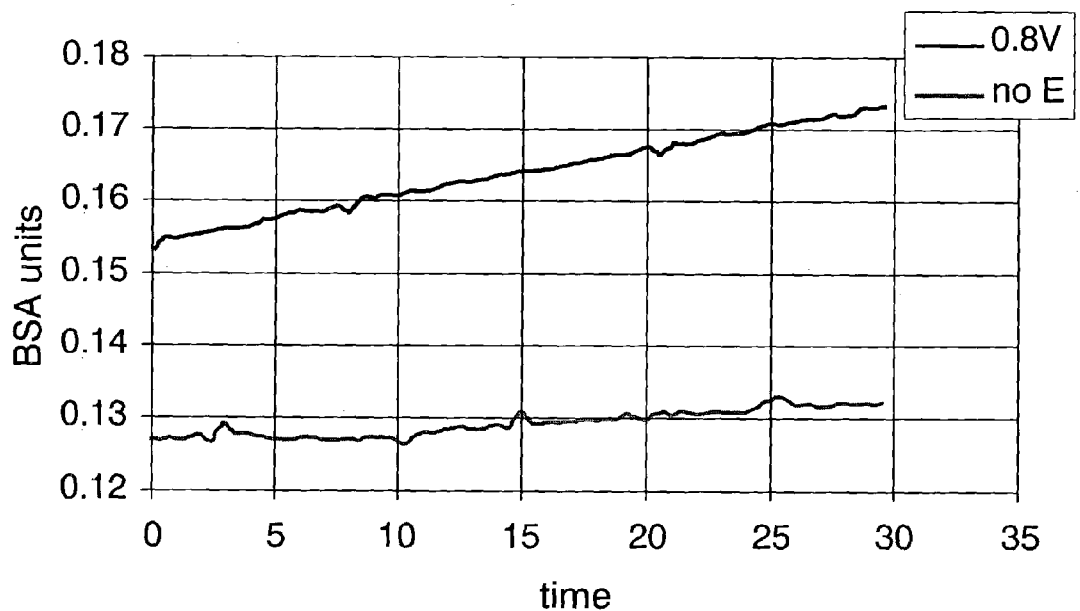
FIG. 2 is an absorbance vs. time curve that shows selective deposition of colloidal gold on transparent electrodes of Indium-Tin Oxide (ITO) (see Example 2).

This example illustrates the selective deposition of colloidal gold on transparent electrodes of ITO. For this purpose, a colloidal gold suspension [Sigma, reference: G-1652 (gold colloid, 20 nm)] was put in contact with the ITO transparent electrodes. The deposition was done applying +0,8V (vs. Ag/AgCl saturated) for 30 minutes. As control were used electrodes on which potential was not applied. The colloidal gold deposition on the electrodes was characterised by spectrophotometry, monitoring in real time the absorbance at the colloidal gold characteristic wavelength (523 nm), deposited on the electrode. The obtained results are shown in FIG. 2, on which a more pronounced slope can be observed corresponding to the electrode on which potential was applied (0.8V), indicating the colloidal gold selective deposition in that electrode compared to the control (not polarised).

EXAMPLE 3

This example illustrates the selective deposition of DOTCG conjugates on electrodes obtained through the screen printing technique.

The DOTCG conjugates were prepared according to the process described by Storhoff and collaborators [Storhoff et al. (1998), Journal of the American Chemical Society, 120: 1959–1964]. For this purpose, a colloidal gold commercial solution was added (CG) [Sigma, reference: G-1652 (gold colloid, 20 nm)] to a DOT solution and was mixed, in such a way that the final concentrations in the DOTCG conjugate were $2,54 \times 10^{12}$ particles $mL^{-1}$ of colloidal gold of 20 nm and 3 µM of DOT. The mixture was left to react for 24 hours at room temperature and in the dark. Immediately after, the mixture was centrifuged at 5.000 rpm and 4° C. for 90 minutes. The supernatant was removed and the solid was redissolved in histidine buffer 50 mM, pH 7.5 (first wash). It was centrifuged for the second time under the same conditions, the supernatant was removed and the solid was redissolved in histidine buffer 50 mM, pH 7.5. The absorbance spectrum was monitored (ABS) to check that no aggregates had been formed.

Figure 3:
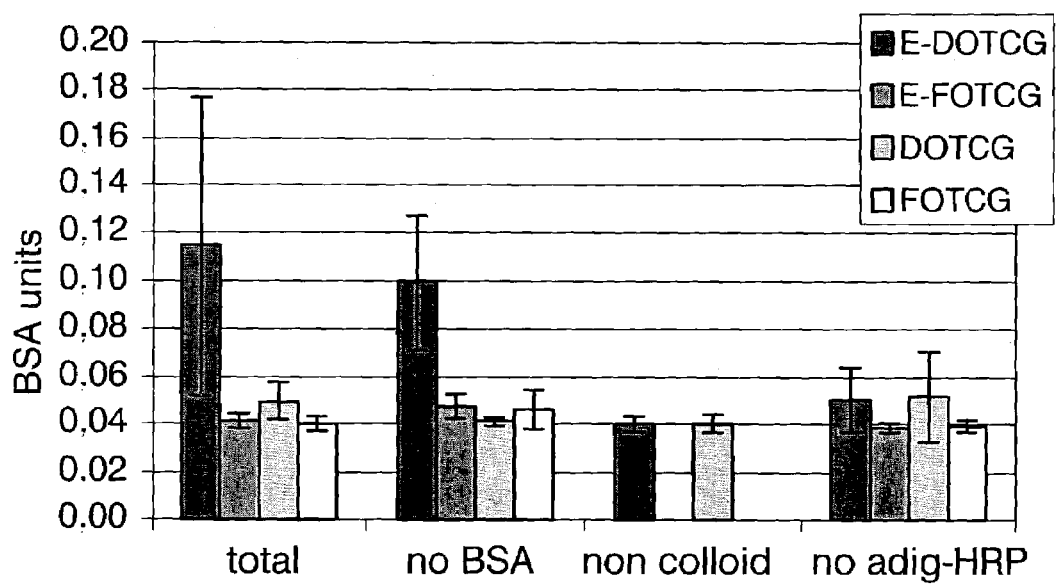
FIG. 3 shows the selective deposition of colloidal gold conjugates with an oligonucleotide of sequence 5'-AGCCAGCTGAGCCAATTCA-3'(SEQ ID NO: 2 in the accompanying "Sequence Listing") modified with a sequence 3' dioxigenin(dig) and a sequence 5' thiol group (SH) (DOT), as of now abbreviated as DOTCG, on electrodes obtained through the screen printing technique (see Example 3). Once the electrodes have been blocked with bovine serum albumin (BSA), they were incubated in an antidigoxigenin-peroxidase solution (antidig-HRP) and subsequently, after introduction of the tetramethylbenzidine me substrate (TMB) the colourimetric response was measured. Electrodes without applied potential, electrodes with conjugate FOTCG and electrodes without BSA (no BSA), without colloid (no colloid) or without antidigoxigenin-peroxidase (no adig-HRP) were used as controls.

For the deposition of that conjugate, 0.5 µL of DOTCG solution were put in contact with those electrodes obtained by the screen printing technique and +1.2V (vs. Ag/AgCl saturated) were applied for 2 minutes. In continuation, the electrodes were blocked by incubation in a (BSA) solution and subsequently were incubated in an antidigoxigenin-peroxidase solution (antidig-HRP). The colourimetric response was measured after incubation with tetramethyllbenzidine substrate (TMB). Different controls were performed: the electrodes which had no potential applied, electrodes with FOTCG conjugate and electrodes without BSA (no BSA), without colloid (no colloid) or without antidigoxigenine-peroxidase (no adig-HRP). The obtained results are shown on FIG. 3. The absorbance values were significantly higher for the electrodes on which DOTCG was used and potential was applied and demonstrate the selective deposition of the conjugate and, also, the digoxigenin functionality (affinity recognition).

EXAMPLE 4

This example illustrates the selective deposition of DOTCG conjugates over electrodes obtained through the screen printing technique and the maintenance of their biorecognition functionality (through hybridisation). Furthermore, they demonstrate an electrochemical method to detect the affinity reaction.

Figure 4:
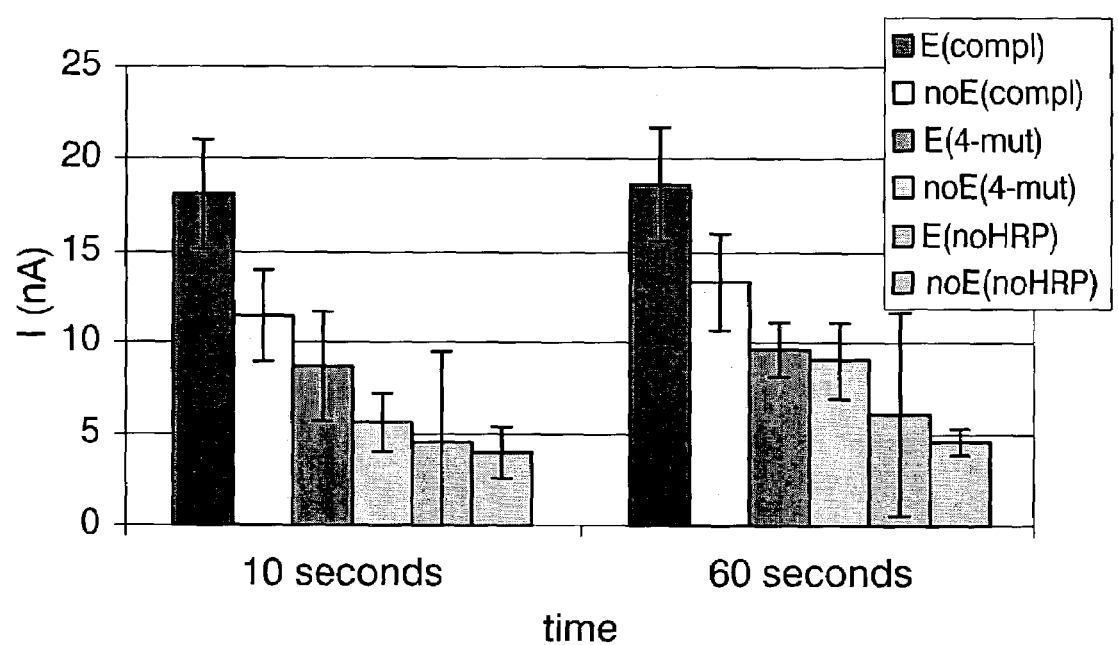
FIG. 4 shows the selective deposition of conjugates DOTCG on electrodes obtained through the screen printing technique and their subsequent hybridization (see Example 4). Once the deposition had been effected, hybridization was done with the complementary sequence oligonucleotide 5'-TGAATTGGCTCAGCTGGCT-3'(SEQ ID NO: 3 in the accompanying "Sequence Listing") (compl) or with the nucleotide of that sequence with 4 mutations 5'-TGAGTGGGCTCGGGTGGCT-3'(SEQ ID NO: 4 in the accompanying "Sequence Listing") (4mut) modified with biotine in 5'. Further on the electrodes were incubated in streptavidin-peroxidase solution (estrav-HRP) and the electrochemical response was measured in the presence of $H_2O_2$ with osmium complexes as mediators. Electrodes which had no potential applied (no E) and electrodes without streptavidin-peroxidase (no HRP) were used as a control. The current intensities were measured at different times (10 and 60 seconds).

The DOTCG conjugates were prepared according to the process described in the Example 3. The deposition of DOTCG conjugated consisted in placing 0.5 µL of conjugate DOTCG solution over those electrodes obtained through the screen printing techique and in the application of +1.2V (vs. Ag/AgCl saturated) for 2 minutes. In continuation, the hybridization was done at 55° C. with complementary sequences (compl) or with sequences having 4 mutations (4-mut) modified with biotin at 5'. Subsequently, the electrodes were incubated in a streptavidin-peroxidase solution (estrav-HRP). The electrochemical response was measured in the presence of $H_2O_2$ with osmium complexes as electron mediators. Different controls were performed: electrodes on which no potential was applied (no E) and electrodes without streptavidin-peroxidase (no HRP). The current intensities were measured at different times (10 and 60 seconds). The obtained results are shown in FIG. 4, where can be observed that the electrodes on which hybridisation was done with the complementary sequence gave higher current intensities than the electrodes on which the hybridisation was done with the sequence of 4 mutations. The electrodes that had potential applied gave higher current intensities than the electrodes that had no potential applied. The current intensities, significantly different to the ones without enzyme, demonstrate the selective deposition. This experiment also demonstrates the ability to distinguish between complementary and four-mutated sequences.

The invention claimed is:

1. A method of fabricating a chip for analysis of analytes, comprising the steps of:
   a) putting a multielectrodic chip, lithographed on a wafer that contains between 2 and 2000 individually polarizable electrodes, in direct contact with a solution or suspension that comprises modified colloidal particles modified with a chemical or biochemical recognition element;
   b) applying to one electrode of said chip, a potential between −1 and +2V (vs. Ag/AgCl saturated) for a period of time between 1 and 300 seconds, so that the colloid modified with the chemical or biochemical recognition element is deposited selectively and with micrometric resolution, over the electrode on which the potential has been applied;
   c) washing the chip after step b); and
   d) repeating steps a), b) and c) in order to deposit the chemical or biochemical recognition element, equal or different to the one or the ones previously deposited, on each of the electrodes of the chip.

2. The method according to claim 1, in which the colloidal particles included in the solution or suspension that comes in contact with the multielectrodic chip comprise gold, silver, cadmium, glass, latex or polyurethane modified colloidal particles.

3. The method according to claim 1, in which the potential applied on the electrode is between 0 and +1V, vs. Ag/AgCl saturated.

4. The method according to claim 1, in which the period of time during which the potential is applied on the electrode is between 1 and 10 seconds.

5. The method according to claim 1, in which the solution and suspension that includes the colloid modified with a chemical or biochemical recognition element is applied by a microfluidic device.

6. The method according to claim 1, in which the chemical or biochemical recognition element is selected among chemical, biochemical or biological products.

7. The method according to claim 6, in which that chemical or biochemical recognition element is selected from aptamers, molecular tweezers, genetically modified enzymes, synthetic nucleic acids, crown esters, molecularly-imprinted polymers, enzymes, antibodies, nucleotide sequences, receptors or cells.

8. The method according to claim 1, in which the colloidal modified with a chemical or biochemical recognition element enters into a solution or suspension in an aqueous, organic or aquo-organic media.

9. The method according to claim 8, in which the solution is an aqueous solution or a high dielectric organic solvent solution with ionic strength lower or equal to 0.3 M.

* * * * *

SEQUENCE LISTING

```
<160> NUMBER OF SEQ ID NOS: 4

<210> SEQ ID NO 1
<211> LENGTH: 44
<212> TYPE: DNA
<213> ORGANISM: artificial sequence
<220> FEATURE:
<223> OTHER INFORMATION: chemically synthesized
<220> FEATURE:
<221> NAME/KEY: modified_base
<222> LOCATION: 1
<223> OTHER INFORMATION: base modified with a thiol group
<220> FEATURE:
<221> NAME/KEY: misc_binding
<222> LOCATION: 44
<223> OTHER INFORMATION: bonded to fluoresceine isothiocyanate

<400> SEQUENCE: 1
cccccccccc ccttttttttt tttttttttt ttcccccccc cccc            44

<210> SEQ ID NO 2
<211> LENGTH: 19
```

```
<212> TYPE: DNA
<213> ORGANISM: artificial sequence
<220> FEATURE:
<223> OTHER INFORMATION: chemically synthesized
<220> FEATURE:
<221> NAME/KEY: modified_base
<222> LOCATION: 1
<223> OTHER INFORMATION: base modified with a thiol group
<220> FEATURE:
<221> NAME/KEY: misc_binding
<222> LOCATION: 19
<223> OTHER INFORMATION: bonded to digoxygenin

<400> SEQUENCE: 2
agccagctga gccaattca                                              19

<210> SEQ ID NO 3
<211> LENGTH: 19
<212> TYPE: DNA
<213> ORGANISM: artificial sequence
<220> FEATURE:
<223> OTHER INFORMATION: complementary oligonucleotide to SEQ. ID. No: 2
      for hybridization
<220> FEATURE:
<221> NAME/KEY: misc_binding
<222> LOCATION: 1
<223> OTHER INFORMATION: bonded to biotin

<400> SEQUENCE: 3
tgaattggct cagctggct                                              19

<210> SEQ ID NO 4
<211> LENGTH: 19
<212> TYPE: DNA
<213> ORGANISM: artificial sequence
<220> FEATURE:
<223> OTHER INFORMATION: complementary oligonucleotide to SEQ. ID. No: 2
      for hybridization
<220> FEATURE:
<221> NAME/KEY: misc_binding
<222> LOCATION: 1
<223> OTHER INFORMATION: bonded to biotin

<400> SEQUENCE: 4
tgagtgggct cgggtggct                                              19
```